US009717479B2

(12) United States Patent
Palti

(10) Patent No.: US 9,717,479 B2
(45) Date of Patent: Aug. 1, 2017

(54) PASSIVE DATA TRANSMISSION

(71) Applicant: Yoram Palti, Haifa (IL)

(72) Inventor: Yoram Palti, Haifa (IL)

(*) Notice: Subject to any disclaimer, the term of this patent is extended or adjusted under 35 U.S.C. 154(b) by 256 days.

(21) Appl. No.: 14/454,858

(22) Filed: Aug. 8, 2014

(65) Prior Publication Data
US 2015/0045669 A1 Feb. 12, 2015

Related U.S. Application Data

(60) Provisional application No. 61/864,216, filed on Aug. 9, 2013.

(51) Int. Cl.
*A61B 8/08* (2006.01)
*A61B 5/00* (2006.01)
*A61B 8/06* (2006.01)
*G01S 7/00* (2006.01)
*A61B 5/0215* (2006.01)
*A61B 8/00* (2006.01)
*A61B 8/12* (2006.01)

(52) U.S. Cl.
CPC ............ *A61B 8/488* (2013.01); *A61B 5/0015* (2013.01); *A61B 5/0028* (2013.01); *A61B 5/0031* (2013.01); *A61B 5/0215* (2013.01); *A61B 8/06* (2013.01); *A61B 8/52* (2013.01); *A61B 8/56* (2013.01); *G01S 7/003* (2013.01); *A61B 5/0024* (2013.01); *A61B 8/12* (2013.01); *A61B 2560/0219* (2013.01)

(58) Field of Classification Search
CPC .......... A61B 2560/0219; A61B 5/0015; A61B 5/0024; A61B 5/0028; A61B 5/0031
See application file for complete search history.

(56) References Cited

U.S. PATENT DOCUMENTS

| 6,585,647 B1 * | 7/2003 | Winder | A61B 8/08 128/916 |
| 6,802,811 B1 * | 10/2004 | Slepian | A61B 5/0031 600/309 |
| 2008/0021289 A1 | 1/2008 | Zhang et al. | |

(Continued)

OTHER PUBLICATIONS

Dehollain, C., Dr., et al., "In vivo ULTRAsonic Transponder System for Biomedical Applications FP7 Collaborative Project," Strep ULTRAsponder, Ecole Polytechnique Fédérale de Lausanne (EPFL), RFIC Group, Apr. 5, 2011, 27 pages.

(Continued)

*Primary Examiner* — Baisakhi Roy
(74) *Attorney, Agent, or Firm* — Potomac Law Group, PLLC

(57) ABSTRACT

Data is communicated from an implanted section to an external location. The implanted section includes a transducer such as a piezoelectric element with an ultrasound reflecting surface that moves in response to an applied driving signal. A sensor generates an output signal that depends on a sensed parameter, and a control circuit drives the transducer based on the sensor's output. The transducer's response to the driving signal is repeatable such that the value of the output signal can be determined by measuring the variations in the velocity of the surface using externally applied Doppler ultrasound, and computing the value of the sensor's output from the measured variations in velocity.

15 Claims, 2 Drawing Sheets

(56) References Cited

U.S. PATENT DOCUMENTS

2013/0303910 A1* 11/2013 Hubbard .......... A61B 8/06
600/443
2014/0147013 A1* 5/2014 Shandas .......... A61B 8/481
382/107

OTHER PUBLICATIONS

Mari, J.M., et al., "Detection of deeply implanted impedance-switching devices using ultrasound doppler," IEEE Transactions on Ultrasonics Ferroelectrics and Frequency Control, IEEE, US, vol. 60, No. 6, Jun. 1, 2013, pp. 1074-1083.

Mari, J.M., et al., "Detection of deeply implanted impedance-switching devices using ultrasound doppler," French Institute of Health and Medical Research, Ultrasponder, 16 pages, undated.

Mazzilli, F., et al., "In-vitro platform to study ultrasound as source for wireless energy transfer and communication for implanted medical devices," 2010 Annual International Conference of the IEEE Engineering in Medicine and Biology Society: (EMBC 2010); Buenos Aires, Argentina, Aug. 31-Sep. 4, 2010, IEEE, Piscataway, NJ, USA, Aug. 31, 2010, pp. 3751-3754.

Mazzilli, F., et al., "Ultrasound for Wireless Energy Transfer and Communication for Implanted Medical Devices," Ecole Polytechnique Fédérale de Lausanne (EPFL), RFIC Group, Seville, Sep. 17, 2010, 28 pages.

Peisino, M., "Deeply implanted medical device based on a novel ultrasonic telemetry technology," Ecole Polytechnique Fédérale de Lausanne, May 17, 2013, 142 pages.

Palti, Y., et al., "Pulmonary Doppler Signals: a Potentially New Diagnostic Tool," Eur. J. Echocardiography (2011), 5 pages.

Palti, Y., et al., "Footprints of Cardiac Mechanical Activity as Expressed in Lung Doppler Signals," Echocardiography, (2014).

Search Report and Written Opinion in corresponding PCT/IB2014/002540, dated Apr. 7, 2015, 13 pages.

* cited by examiner

PASSIVE DATA TRANSMISSION

CROSS REFERENCE TO RELATED APPLICATIONS

This Application claims the benefit of U.S. Provisional Application 61/864,216, filed Aug. 9, 2013, which is incorporated herein by reference in its entirety.

BACKGROUND

This invention relates to communication between two or more devices positioned at a distance from each other, where power consumption is a limiting factor.

One example where this can occur would be transmitting data gathered by a battery-powered sensor that is implanted within the human body to the outside world over a long period of time. In this example, especially when continuous monitoring and transmission is being made of physiological, chemical or physical parameters, the battery power may not be sufficient for the transmission to continue for a sufficiently long time when data transmission is implemented using conventional techniques. As a result, the battery may require replacement by an invasive procedure.

Another example is when data or instructions/commands are to be transmitted from one point within a body to a second point in the same body. For example, it may be desirable to have a sensor that measures pulmonary vein blood pressure transmitted pressure data to a cardiac pacemaker in order to optimize the pacemaker's performance. Once again, battery power may not be sufficient and the battery may require replacement by an invasive procedure.

Examples of using ultrasound to detect an implanted device are described in *Detection of Deeply Implanted Impedance-Switching Devices Using Ultrasound Doppler* by J. M Mari et al, IEEE Transactions on Ultrasonics, Ferroelectrics, and Frequency Control, vol. 60, no. 6, June 2013, at 1074-1083. This article is incorporated herein by reference in its entirety.

Examples of using ultrasound to communicate with an implanted device are described in *Deeply Implanted Medical Device Based on a Novel Ultrasonic Telemetry Technology* by Michela Peisino, Thèse no 5730, École Polytechnique Fédérale de Lausanne, May 17, 2013. This paper is incorporated herein by reference in its entirety.

Examples of using ultrasound for energy transfer and communication with implanted devices are described in *Ultrasound for Wireless Energy Transfer and Communication for Implanted Medical Devices* by F. Mazzilli and C. Dehollain, ESSCIRC 2010, Workshop, Seville, Sep. 17, 2010. This paper is incorporated herein by reference in its entirety.

But the impedance-switching based technology described in these references is inadequate, and improved approaches for communicating with implanted devices are needed.

SUMMARY OF THE INVENTION

One aspect of the invention is directed to an apparatus that includes an implanted section and an external section. The implanted section includes (a) a transducer having an ultrasound reflecting surface that moves in response to an applied driving signal, wherein variations in the applied driving signal causes corresponding variations in the velocity of the surface, (b) a sensor that generates an output signal that depends on a sensed parameter, and (c) a first control circuit that generates the driving signal that is applied to the transducer based on the output signal generated by the sensor, such that variations in the value of the output signal result in corresponding variations in the driving signal. The transducer's response to an applied driving signal and the first control circuit's response to the output signal are repeatable such that the value of the output signal can be determined by measuring the variations in the velocity of the surface using externally applied Doppler ultrasound. The external section includes (1) an ultrasound transmitter configured to direct ultrasound energy at a carrier frequency onto the transducer, (2) an ultrasound receiver configured to detect ultrasound reflections from the surface that have been shifted in frequency by the moving surface, (3) a Doppler processor configured to determine the velocity of the surface based on the detected reflections, and (4) a second control circuit configured to map the determined velocity onto a value of the sensed parameter.

In some embodiments the transducer is a piezoelectric element. In some embodiments, the implanted section further includes a biocompatible housing, and the transducer, the sensor, and the first control circuit are all housed in the housing. In some embodiments, the first control circuit includes a processor and a driver circuit. In some embodiments, the driving signal is selected to cause FM modulation of the carrier when the surface moves. In some embodiments, the driving signal is a triangular waveform. In some embodiments, the driving signal has a frequency between 50 and 1000 Hz. In some embodiments, the carrier frequency is between 1 and 20 MHz. In some embodiments, the movement of the surface is a vibration.

Another aspect of the invention is directed to a sensing apparatus that includes a transducer having an ultrasound reflecting surface that moves in response to an applied driving signal, wherein variations in the applied driving signal causes corresponding variations in the velocity of the surface. This apparatus further includes a sensor that generates an output signal that depends on a sensed parameter, and a control circuit that generates the driving signal that is applied to the transducer based on the output signal generated by the sensor, such that variations in the value of the output signal result in corresponding variations in the driving signal. The transducer's response to an applied driving signal and the control circuit's response to the output signal are repeatable such that the value of the output signal can be determined by measuring the variations in the velocity of the surface using externally applied Doppler ultrasound.

In some embodiments, the transducer is a piezoelectric element. In some embodiments, the sensing apparatus further includes a biocompatible housing, wherein the transducer, the sensor, and the control circuit are all housed in the housing. In some embodiments, the sensing apparatus further includes a battery that provides power to the sensor and the control circuit, and the battery is housed in the housing. In some embodiments, the control circuit includes a processor and a driver circuit. In some embodiments, the driving signal has a frequency between 50 and 1000 Hz. In some embodiments, the movement of the surface is a vibration.

Another aspect of the invention is directed to a method for communicating with an implanted sensor. This method includes the steps of (1) obtaining an output signal from a sensor, wherein the output signal depends on a sensed parameter; (2) generating, based on the output signal obtained from the sensor, a driving signal for driving a transducer, such that variations in the value of the output signal result in corresponding variations in the driving signal, wherein the driving signal is configured to cause an ultrasound reflecting surface of the transducer to move, and wherein variations in the applied driving signal causes corresponding variations in the velocity of the surface; (3) applying the driving signal to the transducer, wherein the transducer's response to the applied driving signal and the generation of the driving signal based on the output signal obtained from the sensor are repeatable such that the value of the output signal can be determined by measuring the variations in the velocity of the surface using externally applied Doppler ultrasound; (4) directing ultrasound energy at a carrier frequency onto the transducer; (5) detecting ultrasound reflections from the surface that have been shifted in frequency by the moving surface; (6) using Doppler processing to determine the velocity of the surface based on the detected reflections; and (7) mapping the determined velocity onto a value of the sensed parameter.

In some embodiments, the driving signal is selected to cause FM modulation of the carrier when the surface moves. In some embodiments, the driving signal is a triangular waveform. In some embodiments, the driving signal has a frequency between 50 and 1000 Hz. In some embodiments, the carrier frequency is between 1 and 20 MHz. In some embodiments, the movement of the surface is a vibration.

DESCRIPTION OF THE PREFERRED EMBODIMENTS

Figure 1:
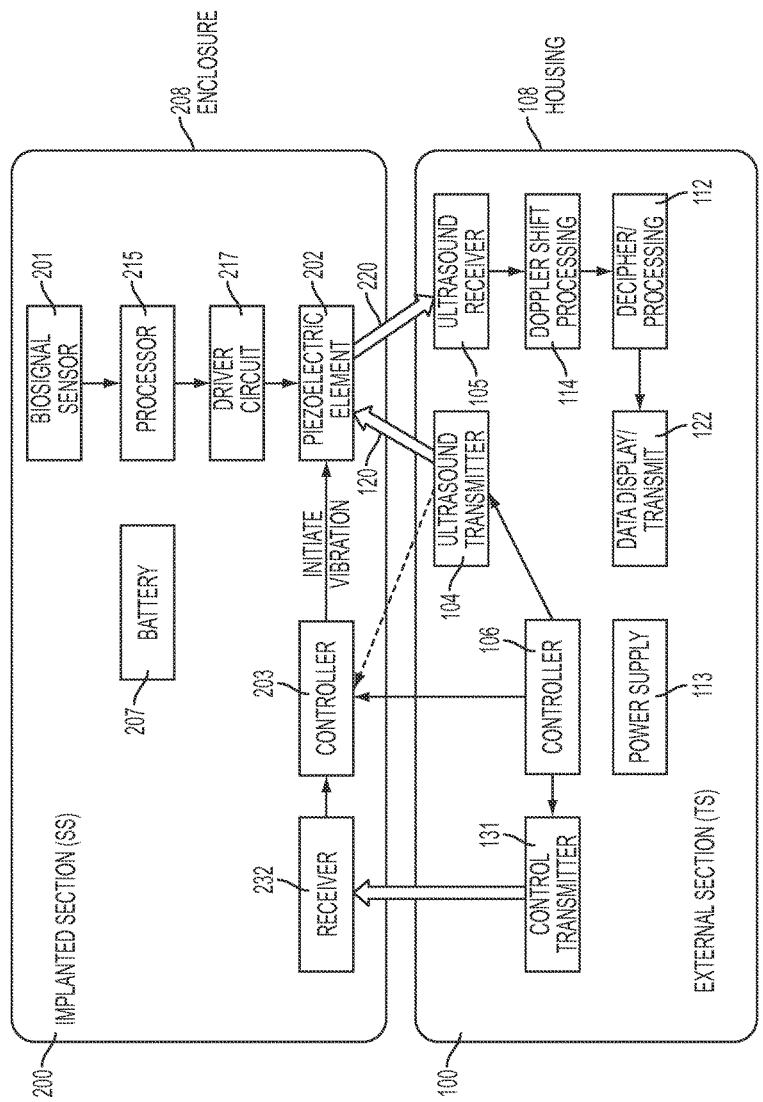
FIG. 1 is a block diagram of a system for communicating with an implanted device.

Referring to FIG. 1, the preferred embodiment uses an implanted device that changes the velocity of an implanted transducer such as a piezoelectric element. The changes in velocity are detected using Doppler ultrasound. This embodiment includes two main sections: an implanted section 200 and an external section 100.

Instead of relying on internally-supplied battery power to transmit a signal from the implanted section to the external section, the preferred embodiments rely on a carrier signal that originates outside the body. The implanted section 200 changes the velocity of an ultrasound reflecting surface of a transducer (e.g., a Piezoelectric Reflecting Element 202, hereinafter "PRE"). When the external section 100 directs an ultrasound beam onto the PRE 202 in the implanted section 200, the changes in velocity of the surface of the PRE 202 causes a frequency shift, and that frequency shift is detected externally. This approach is superior to the prior art mentioned above, which merely changes the impedance of the implanted transducer.

This approach also saves power because modulation of an externally applied signal can be accomplished using less power than it would take to have the implanted section transmit the signal by itself. This reduction in power consumption extends the life of the battery in the implanted section with respect to conventional data transmission modalities.

The Passive Data Transmission System includes one or more implanted sensors designed to measure or monitor physiological, chemical or physical parameters, etc. from the location where sensing can be carried out to either (a) a location outside the patient's body or (b) to another devices that is implanted in a different location in the body.

FIG. 1 depicts a preferred embodiment that includes two main sections: an implanted section 200 and an external section 100. It relies on a transducer (e.g., PRE 202) to modulate ultrasound beams 120 that are generated by the external section and aimed towards the implanted section. In alternative embodiments, other transducers besides piezoelectric reflecting elements may be used to produce the vibrations (e.g., a miniature electromagnetic speaker).

The external section 100 is also referred to herein as the Energizing/Transmitting System (TS) and it preferably includes an ultrasound Doppler transmitter 104 and ultrasound Doppler receiver 105; a processor 114 and 112 that controls the system and deciphers the coded signals; a power supply 113; and a housing 108. The processor preferably includes two processing steps: the first step is Doppler shift processing 114, where the velocity of the surface of the PRE is determined. The second is the decipher processing step 112, where the velocities determined in the first step are mapped onto a value of the sensed parameter. Although depicted as two discrete blocks in FIG. 1, these two processing steps may optionally be implemented by a single processor (not shown). Optionally, a display 122 may be used to display the result of the mapping. Alternatively, the result of the mapping may be transmitted to an external device.

The implanted section 200 is also referred to herein as the sensing system (SS) and it preferably includes a sensor or sensors 201 with associated amplifiers, etc.; a processor 215 configured to control and activate the sensors 201 and to interpret return signals from the sensors; a driver circuit 217 that translates the output of the processor 215 into an electric signal using a modulation scheme (including but not limited to FM, AM or another modulation scheme; a PRE 202 such as a small disc that is activated (i.e. made to move e.g., to vibrate) by the modulated electric signals. All of these components are powered by a suitable power source (e.g., battery 207) and are preferably housed in a biocompatible enclosure 208.

The sensor 201 of the SS 200 senses the relevant biological, chemical, or physical parameter. Any of a wide variety of conventional sensors can be used for this purpose, depending on the anatomical function that is being monitored. Preferably, the sensor 201 transduces the parameter that is being sensed into an electric signal. When necessary, the ensuing electric signals are amplified, filtered, shaped, etc., and the resulting signal is provided to a processor 215 via a suitable interface.

The processor 215 has the ability to drive the PRE 202 by sending appropriate signals (e.g., pulses) to a driver circuit 217, such that when the driver circuit 217 drives the PRE 202 in response to the signals from processor 215, the PRE 202 responds mechanically to the driving signals by moving in a repeatable manner (e.g., by vibrating). Collectively, the processor 215 and the driver circuit 217 make up a control circuit.

The processor 215 encodes desired output data into the signals that control the PRE 202 (where the output data represents information that was obtained from the sensor). The PRE 202 mechanically responds to those signals by moving in a repeatable manner, and the mechanical activity of the PRE 202 is then detected by the external section 100. The system relies on this repeatability to deliver information from the implanted section to the outside world. A preferred way to detect the mechanical activity of the PRE is by using Doppler ultrasound.

Doppler ultrasound is beneficial because it detects velocities. So in order to convey information from the SS 200 to the TS 100, the SS 200 controls the velocity of the PRE 202 contained within the SS 200. To do this, the processor 215 encodes the data that is wants to send outside the body onto a signal that causes the PRE 202 to move (e.g., vibrate) in a repeatable manner. For example, the shape, duration, time line, frequency etc. of a vibration can be used to convey the information that was obtained by the sensor. The vibration of the PRE 202 will then convey all the required information. (Note that the information detected by the Doppler system is preferably contained in the vibrating reflector velocity or the velocity profile with time.)

In one example, the information may be coded in the frequencies of a triangular waveform, in which case the velocity is a square wave of corresponding frequencies. Assuming that the frequency of the signal that is applied to the PRE 202 is kept constant, increasing the amplitude of a triangular waveform that drives the PRE will increase the amplitude of the mechanical vibrations. This will increase the velocity of the PRE 202 as it passes through the midpoint of the vibration. This increased velocity can then be picked up by the TS 100.

In another example, the information can be conveyed by generating a series of pulses, and encoding the information onto the pulses. For example, a wide pulse can represent a 1 and a narrow pulse can represent a 0. Alternatively, a pulse can represent a 1 and the absence of a pulse can represent a 0. A wide variety of alternative modulation schemes can be readily envisioned.

The motion of the ultrasound reflecting surface of the PRE 202 (e.g., the vibrations) can then be detected by the TS 100, using Doppler ultrasound in a conventional manner. For example, in the embodiment depicted in FIG. 1, the TS 100 is positioned on the body surface such that it can easily be provided with the necessary power. The TS 100 in this embodiment is an ultrasound Doppler system, preferably without imaging (e.g., a 2 MHz pulsed Doppler system). In alternative embodiments, other frequencies may be used, e.g., between 1 and 20 MHz.

An ultrasound transmitter 104 emits a wave/beam 120, and that beam is directed at the selected SS 200. Ultrasound energy 220 is reflected back from the PRE 202 in the SS 200. As explained above, the velocity of the moving surface of the PRE 202 will depend on the signals that are applied to the PRE 202 within the SS 200. As a result, the ultrasound energy 220 reflected back from the PRE 202 will be shifted in frequency (i.e., Doppler shifted) by the motion of the PRE 202. (Note that since the PRE 202 moves in response to the encoded data, that movement can be detected, and the data can be extracted from the detected movements.) The Doppler shifts are picked up by the ultrasound receiver 105 and the Doppler shifts are isolated and processed in block 114 to determine the velocity of the surface of the PRE.

Decipher processing 112 is then implemented, where the determined velocities are mapped onto a driving signal waveform that is known to produce the velocities that are measured. Then, the driving waveform can be mapped onto the value of the sensed parameter based on knowledge of which driving waveforms are generated by the driver circuit 217 in response to a given output levels from the sensor 201. In other words, because the TS 100 is aware of the transfer function of the sensor 201, the processor 215, and the driver circuit 217, and can compute the value of the sensed parameter from the measured velocities in the Decipher processing block 112. Decipher processing 112 is preferably implemented in a control circuit such as a processor, e.g., using a lookup table to map the determined velocities onto values of the sensed parameters.

Optionally, the resulting data can then be displayed or transmitted.

The coded vibration velocities are thereby translated so as to deliver the Sensor-derived information (i.e., the value of the sensed parameter) to the outside world. The information thus obtained can be displayed, transmitted to the physician, a medical unit, another implanted device that uses it to adjust its function, etc. in any conventional manner.

As an example, the system depicted in FIG. 1 may be used to transmit data from a blood pressure sensor implanted in an artery to a Receiver positioned on the body surface. In this case, the sensor 201 would be a pressure transducer that transduces the blood pressure into an electric voltage that depends on the pressure. The sensor may be configured to detect the systolic and/or diastolic pressures (e.g., refreshed every 3-10 sec). Alternatively, the whole pulse wave contour can be sensed, e.g., with pressure values obtained at a rate of 20-100 Hz. In this example, the output of the sensor 201 is an analog signal. The analog signal is then digitized and fed to the processor 215.

The processor 215 transforms the digitized voltage into a coded voltage waveform such that its frequency or other characteristics of the waveform varies with time in correspondence to the pressure values that were sensed by the sensor 201. This waveform is applied to the driver circuit 217, which generates a driving signal that drives the PRE 202 and causes the PRE to vibrate accordingly. The driving signal preferably has a frequency content that is within the range of the frequency response of the PRE 202.

The sensed pressure is preferably coded using a code that is imparted onto the velocity of movement of the PRE 202, rather than its amplitude, etc. For example, if the driving signal has a triangular waveform, the velocity that is detected using Doppler will be a square wave of the same periodicity. In such a case the coding can be in the duration of individual triangular wave cycle times. A repeatable mapping is used (e.g., 100 microsecond of pulse width of per millivolt of signal from the sensor). Different voltages from the sensor will therefore be registered as square waves of different duration. This is a form of frequency modulation.

Alternatively, the slopes of the triangular waves can be changes, which will increase the velocity of the PRE, and will therefore be registered as square waves of different amplitude, i.e. an amplitude modulation code. The information can also be coded in the duration or shape of a burst of waves or vibration.

The Doppler registered velocity is obtained by a TS 100 that is preferably positioned at the surface of the body using an appropriate ultrasound impedance matching gel between the TS 100 and the body. A standard Doppler ultrasound system, preferably pulse Doppler, includes the transmitter 104. The ultrasound beam, for example 2 MHz, is aimed at the PRE 202, and the PRE reflects the beam.

The vibration or movement of the ultrasound reflecting surface of the PRE 202 will cause a Doppler shift in the 2 MHz waveform that is reflected back to the receiver 105 (which is also included in the standard Doppler ultrasound system). Using conventional Doppler technology by means of an analogue mixer or digital arithmetic tools the shift in frequency from the original wave is extracted from the combined waveform. These waveforms contain the encoded information.

The SS 200 can function independently as explained above under control of the Controller 203. Alternatively, it can be activated and controlled by signals from the TS 100 where Controller 106 determines the activity protocol. The transmission of the commands etc. from the controller 106 in the TS 100 to the controller 203 in the SS 200 may be implemented using any conventional communication modality by employing a control transmitter 131 in the TS 100 and a corresponding receiver 232 in the SS 200. For example, ultrasound, magnetic field or RF (e.g., Bluetooth) may be transmitted by Control Transmitter 131 in the TS 100 and received by Receiver 232 in the SS 200 to communicate.

In some embodiments, the PRE 202 can be integrated into the receiver 232. The SS 200 can also be activated by means of a remote control. When the relevant information can be derived in a relatively short time and is required only periodically, for example every 5 min, the reflector can be activated periodically at predetermined times and the transmitter can be synchronized to this periodicity.

In applications where the sensor reporting requires only a relatively small duty cycle, the TS transmission to PRE 202 can be utilized to generate electric currents that charge the SS battery 207 (and/or a capacitor, (not shown). The delivery of power in this mode is described in the Mazzilli reference identified above, which is incorporated herein by reference. Alternatively, other piezoelectric elements that do not act as reflectors can be used for a similar purpose (i.e., harvesting energy).

The PRE 202 preferably has a very high impedance and is activated by low voltages so as to consume an extremely low current such that it will not drain the SS battery. Furthermore, as the piezo impedance is an inverse function of frequency, low frequency waveforms for activating the vibration of the PRE 202 may be preferable. The PRE 202 may optionally be coated by a highly reflective material (having a sound velocity very different from that of tissues). Preferably, no air (including lung tissue that contains air) should intervene between the PRE 202 and the tissues separating it from the TS 100, since air will dampen the vibration signal and strongly attenuate the ultrasound beam.

Note that in the embodiments described herein, the PRE 202 does not generate a propagating wave itself Instead, it modulates an incoming signal. Advantageously, very low power is required because the power consumption of the implanted SS 200 will relate only to the sensing itself and to the activation of the PRE 202 (i.e., causing the PRE to move so that the motion will shift the frequency with respect to the incoming ultrasound beam), and not to actually transmit the data to the outside world.

Note that the SS 200 is preferably implanted at an orientation such that the
PRE 202 faces the ultrasound beam generated by the TS 100.

Figure 2:
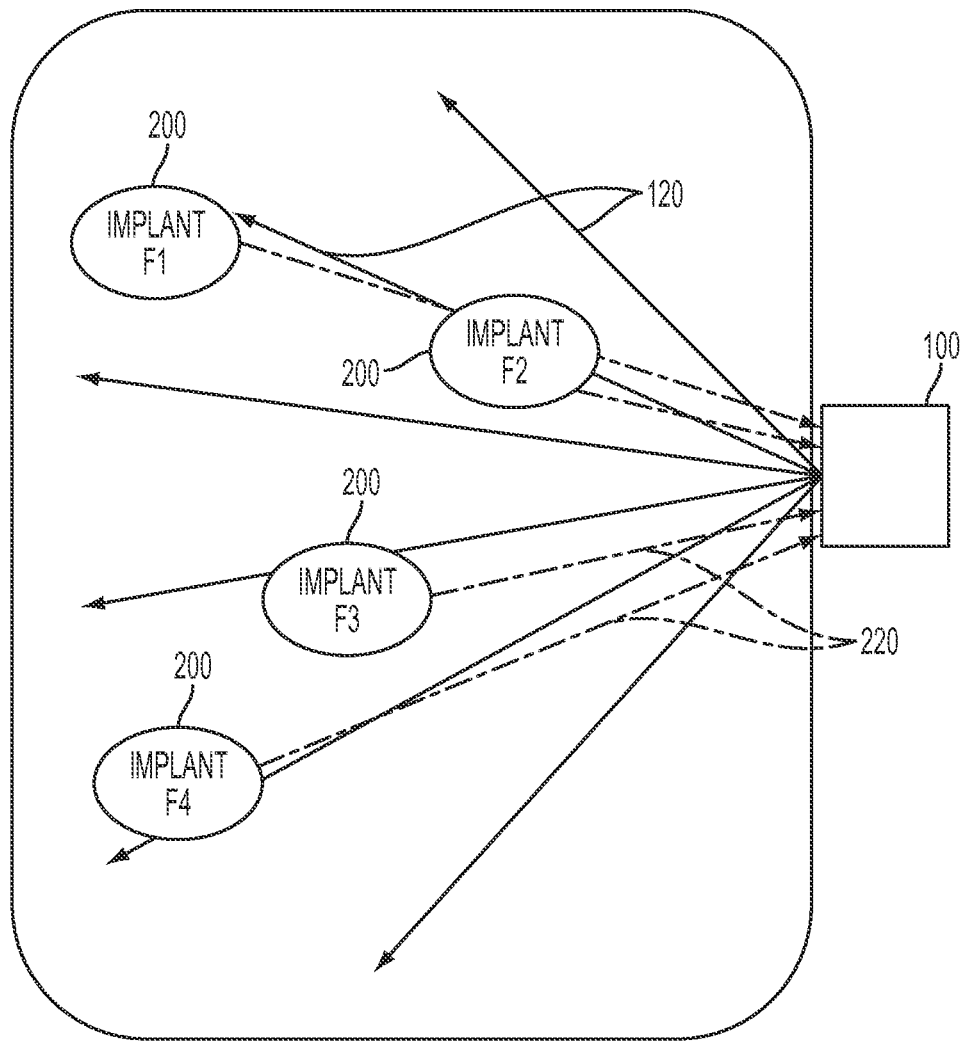
FIG. 2 is a block diagram of communication with a plurality of implanted devices.

Note that a large number of SS 200 implants may be distributed in a single body, as depicted in FIG. 2 (e.g., F1 through F4). The TS 100 directs ultrasound energy 120 at a carrier frequency onto the piezoelectric elements contained in each SS 200, so that changes of the velocity of a surface of the piezoelectric element shifts the frequency with respect to the carrier. The TS 100 then detects the frequency shifted ultrasound reflections 220 from the SS 200. Note that a plurality of SS devices 200 can even be read simultaneously by a single TS 100 provided that in each the sensed information is coded with different frequencies.

Note that Structures such as bone or air filled lung can interfere with ultrasound imaging due to scattering. But Doppler measurements are possible in spite of the scattering and attenuation, as explained in Y. Palti et al. *Pulmonary Doppler Signals: a Potentially New Diagnostic Tool* Eur. J. Echocardiography 12; 25-31 (2011) and Y. Palti et al. *Footprints of cardiac mechanical activity as expressed in lung Doppler signals*, Echocardiography, in press (2014).

Note that while the preferred embodiment described above utilizes ultrasound beams, other waves, such as RF, can replace the ultrasound in less preferred embodiments. However, those other waves are less preferable than ultrasound because the attenuation for RF is 60-90 dB (at 2.45 GHz) and the attenuation for magnetic fields it is 50 dB (at 1 MHz), as compared to the ultrasound which has a relatively low attenuation. More specifically, the attenuation of ultrasound in a living body over a typical distance of 10-20 cm, should be only 8-16 dB (at 1 MHz). In addition, Doppler processing is common for ultrasound.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus, comprising:
   an implanted section that includes
   (a) a sensor that generates an output signal that depends on a sensed parameter,
   (b) a first control circuit that generates a driving signal based on the output signal generated by the sensor, such that variations in the value of the output signal result in corresponding variations in the driving signal, and
   (c) a transducer having an ultrasound reflecting surface that moves in response to the driving signal applied by the first control circuit, wherein variations in the applied driving signal cause corresponding variations in the velocity of the surface,
   wherein the transducer's response to the applied driving signal and the first control circuit's response to the output signal are repeatable such that the value of the output signal can be determined by measuring the variations in the velocity of the surface using externally applied Doppler ultrasound; and
   an external section that includes
   (1) an ultrasound transmitter configured to direct ultrasound energy at a carrier frequency onto the transducer,
   (2) an ultrasound receiver configured to detect ultrasound reflections from the surface that have been shifted in frequency by the moving surface,
   (3) a Doppler processor configured to determine the velocity of the surface based on the detected reflections, and
   (4) a second control circuit configured to map the determined velocity onto a value of the sensed parameter.

2. The apparatus of claim 1, wherein
the transducer comprises a piezoelectric element.

3. The apparatus of claim 1, wherein
the implanted section further comprises a biocompatible housing, wherein the transducer, the sensor, and the first control circuit are all housed in the housing.

4. The apparatus of claim 1, wherein the first control circuit comprises a processor and a driver circuit.

5. The apparatus of claim 1, wherein the driving signal is selected to cause FM modulation of the carrier when the surface moves.

6. The apparatus of claim 1, wherein the driving signal comprises a triangular waveform.

7. The apparatus of claim 1, wherein the driving signal has a frequency between 50 and 1000 Hz.

8. The apparatus of claim 1, wherein the carrier frequency is between 1 and 20 MHz.

9. The apparatus of claim 1, wherein the movement of the surface comprises a vibration.

10. A method for communicating with an implanted sensor, the method comprising the steps of:
 obtaining an output signal from a sensor, wherein the output signal depends on a sensed parameter;
 generating, based on the output signal obtained from the sensor, a driving signal for driving a transducer, such that variations in the value of the output signal result in corresponding variations in the driving signal, wherein the driving signal is configured to cause an ultrasound reflecting surface of the transducer to move, and wherein variations in the applied driving signal causes corresponding variations in the velocity of the surface;
 applying the driving signal to the transducer, wherein the transducer's response to the applied driving signal and the generation of the driving signal based on the output signal obtained from the sensor are repeatable such that the value of the output signal can be determined by measuring the variations in the velocity of the surface using externally applied Doppler ultrasound;
 directing ultrasound energy at a carrier frequency onto the transducer;
 detecting ultrasound reflections from the surface that have been shifted in frequency by the moving surface;
 using Doppler processing to determine the velocity of the surface based on the detected reflections; and
 mapping the determined velocity onto a value of the sensed parameter.

11. The method of claim 10, wherein the driving signal is selected to cause FM modulation of the carrier when the surface moves.

12. The method of claim 10, wherein the driving signal comprises a triangular waveform.

13. The method of claim 10, wherein the driving signal has a frequency between 50 and 1000 Hz.

14. The method of claim 10, wherein the carrier frequency is between 1 and 20 MHz.

15. The method of claim 10, wherein the movement of the surface comprises a vibration.

\* \* \* \* \*